United States Patent
Kramer (10) Patent No.: US 11,445,960 B2
(45) Date of Patent: Sep. 20, 2022

(54) ELECTROGRAPHY SYSTEM EMPLOYING LAYERED ELECTRODES FOR IMPROVED SPATIAL RESOLUTION

(71) Applicant: Trustees of Boston University, Boston, MA (US)

(72) Inventor: Mark Alan Kramer, Cambridge, MA (US)

(73) Assignee: Trustees of Boston University, Boston, MA (US)

( * ) Notice: Subject to any disclaimer, the term of this patent is extended or adjusted under 35 U.S.C. 154(b) by 83 days.

(21) Appl. No.: 17/064,691

(22) Filed: Oct. 7, 2020

(65) Prior Publication Data

US 2021/0106268 A1 Apr. 15, 2021

Related U.S. Application Data

(60) Provisional application No. 62/912,720, filed on Oct. 9, 2019.

(51) Int. Cl.
*A61B 5/245* (2021.01)
*A61B 5/291* (2021.01)
(Continued)

(52) U.S. Cl.
CPC .............. *A61B 5/245* (2021.01); *A61B 5/256* (2021.01); *A61B 5/291* (2021.01); *A61B 5/296* (2021.01); *A61B 5/72* (2013.01)

(58) Field of Classification Search
None
See application file for complete search history.

(56) References Cited

U.S. PATENT DOCUMENTS 4,736,751 A * 4/1988 Gevins ................... A61B 5/369
600/545
5,119,816 A * 6/1992 Gevins ................... G01R 33/28
600/386

(Continued)

FOREIGN PATENT DOCUMENTS

WO WO-9207509 A1 * 5/1992 ......... A61B 5/04085
WO WO-2014205356 A2 * 12/2014 ......... A61B 5/04004

OTHER PUBLICATIONS

Thompson et al., Improved spatial resolution and electrogram wave direction independence with the use of an orthogonal electrode configuration, J Clin Monit Comput (2014) 28:157-163 (Year: 2014).*

(Continued)

*Primary Examiner* — Carl H Layno
*Assistant Examiner* — Manolis Pahakis
(74) *Attorney, Agent, or Firm* — BainwoodHuang (57) ABSTRACT

An electrography system includes an array of conductive electrodes configured to be arranged into two or more spatially separated layers and generate respective electrode signals collectively conveying surface-parallel components and surface-orthogonal components of a pattern of physiological electrical activity sensed by the electrodes. The system further includes signal processing circuitry configured and operative to receive the electrode signals and to generate, based on the surface-parallel and surface-orthogonal components, a set of electrography signals representing the pattern of electrical activity; and a recording component configured and operative to record the electrography signals in a manner enabling application-specific use thereof.

15 Claims, 6 Drawing Sheets

(51) Int. Cl.
  *A61B 5/00* (2006.01)
  *A61B 5/256* (2021.01)
  *A61B 5/296* (2021.01)

(56) References Cited

U.S. PATENT DOCUMENTS

| | | | | |
|---|---|---|---|---|
| 5,331,970 | A * | 7/1994 | Gevins | A61B 5/291 |
| | | | | 600/544 |
| 5,390,110 | A * | 2/1995 | Cheney | G16H 50/50 |
| | | | | 600/407 |
| 5,568,816 | A * | 10/1996 | Gevins | A61B 5/1077 |
| | | | | 600/544 |
| 5,687,724 | A * | 11/1997 | Jewett | G06K 9/0057 |
| | | | | 600/409 |
| 6,032,072 | A * | 2/2000 | Greenwald | A61B 5/291 |
| | | | | 600/397 |
| 6,148,233 | A * | 11/2000 | Owen | A61N 1/0476 |
| | | | | 607/5 |
| 6,356,779 | B1 * | 3/2002 | Katzenmaier | A61N 1/046 |
| | | | | 607/152 |
| 8,112,141 | B2 | 2/2012 | Wilson et al. | |
| 8,615,283 | B2 | 12/2013 | Besio | |
| 8,639,312 | B2 * | 1/2014 | Clark | A61N 1/0556 |
| | | | | 600/373 |
| 9,031,631 | B2 | 5/2015 | Tong et al. | |
| 9,125,581 | B2 * | 9/2015 | Wu | A61B 5/243 |
| 9,294,113 | B2 * | 3/2016 | Feizi-Khankandi | |
| | | | | H03M 1/1265 |
| 9,586,038 | B1 * | 3/2017 | Kosierkiewicz | B32B 7/12 |
| 9,861,802 | B2 * | 1/2018 | Mickelsen | A61M 25/0127 |
| 10,080,505 | B2 * | 9/2018 | Sano | A61B 5/259 |
| 10,238,870 | B2 * | 3/2019 | Pilly | A61B 5/486 |
| 10,444,100 | B2 * | 10/2019 | Dantus | A61B 5/369 |
| 10,912,480 | B2 * | 2/2021 | Sridhar | A61B 5/30 |
| 11,045,132 | B1 * | 6/2021 | Makeyev | A61B 5/291 |
| 2003/0093004 | A1 * | 5/2003 | Sosa | A61B 5/24 |
| | | | | 600/544 |
| 2003/0236466 | A1 * | 12/2003 | Tarjan | A61B 5/25 |
| | | | | 600/508 |
| 2005/0073322 | A1 * | 4/2005 | Hibbs | A61B 5/24 |
| | | | | 324/658 |
| 2005/0119583 | A1 | 6/2005 | Fuller et al. | |
| 2005/0256415 | A1 | 11/2005 | Tan et al. | |
| 2006/0058694 | A1 | 3/2006 | Clark et al. | |
| 2007/0165915 | A1 * | 7/2007 | Fuchs | A61B 5/24 |
| | | | | 382/128 |
| 2007/0270703 | A1 * | 11/2007 | He | G06K 9/0057 |
| | | | | 600/509 |
| 2008/0161708 | A1 | 7/2008 | Kenigsberg et al. | |
| 2008/0161714 | A1 * | 7/2008 | Ahonen | G01R 33/0354 |
| | | | | 600/544 |
| 2009/0054800 | A1 * | 2/2009 | Martinerie | A61B 5/4082 |
| | | | | 600/544 |
| 2009/0093964 | A1 * | 4/2009 | Albera | G06K 9/0057 |
| | | | | 702/14 |
| 2009/0182391 | A1 * | 7/2009 | Fowler | A61N 1/36082 |
| | | | | 607/55 |
| 2010/0274150 | A1 * | 10/2010 | Harlev | A61B 5/349 |
| | | | | 600/523 |
| 2011/0125203 | A1 * | 5/2011 | Simon | A61N 2/006 |
| | | | | 607/2 |
| 2011/0144716 | A1 * | 6/2011 | Bikson | A61N 1/0529 |
| | | | | 607/45 |
| 2011/0184307 | A1 | 7/2011 | Hulin | |
| 2012/0035459 | A1 * | 2/2012 | Revishvili | A61B 5/318 |
| | | | | 600/411 |
| 2012/0150011 | A1 * | 6/2012 | Besio | A61N 1/0476 |
| | | | | 600/372 |
| 2012/0203079 | A1 * | 8/2012 | McLaughlin | A61B 5/316 |
| | | | | 600/377 |
| 2012/0209346 | A1 * | 8/2012 | Bikson | A61N 1/36034 |
| | | | | 607/45 |
| 2012/0296569 | A1 * | 11/2012 | Shahaf | A61B 5/377 |
| | | | | 702/19 |
| 2014/0187973 | A1 * | 7/2014 | Brown | G16H 50/70 |
| | | | | 600/483 |
| 2014/0200429 | A1 * | 7/2014 | Spector | A61B 18/14 |
| | | | | 600/374 |
| 2014/0316217 | A1 * | 10/2014 | Purdon | A61B 5/7275 |
| | | | | 600/300 |
| 2015/0011857 | A1 | 1/2015 | Henson et al. | |
| 2015/0112403 | A1 * | 4/2015 | Ruffini | A61N 1/36025 |
| | | | | 607/45 |
| 2015/0374971 | A1 * | 12/2015 | Dar | A61B 5/6803 |
| | | | | 607/139 |
| 2016/0008632 | A1 * | 1/2016 | Wetmore | A61N 2/006 |
| | | | | 607/45 |
| 2016/0081577 | A1 * | 3/2016 | Sridhar | A61B 5/6803 |
| | | | | 600/383 |
| 2016/0113544 | A1 * | 4/2016 | Li | A61B 5/6833 |
| | | | | 600/391 |
| 2016/0183831 | A1 * | 6/2016 | Rethmeier | A61B 5/274 |
| | | | | 600/394 |
| 2016/0317057 | A1 * | 11/2016 | Li | A61B 5/6833 |
| 2016/0317093 | A1 * | 11/2016 | Berenfeld | A61B 5/068 |
| 2016/0331262 | A1 * | 11/2016 | Kuck | A61N 7/022 |
| 2016/0338611 | A1 * | 11/2016 | Kalinin | A61B 5/6805 |
| 2016/0341684 | A1 * | 11/2016 | Choi | A61B 5/0538 |
| 2016/0354005 | A1 * | 12/2016 | Oakley | A61B 5/6803 |
| 2016/0367189 | A1 * | 12/2016 | Aimone | A61B 5/6831 |
| 2017/0079542 | A1 * | 3/2017 | Spector | A61B 5/35 |
| 2017/0095174 | A1 * | 4/2017 | Fokas | G06T 7/60 |
| 2017/0120041 | A1 * | 5/2017 | Wenger | G16H 50/50 |
| 2017/0188830 | A1 * | 7/2017 | Sankai | A61B 5/7225 |
| 2017/0216595 | A1 * | 8/2017 | Geva | A61B 5/4836 |
| 2017/0296121 | A1 * | 10/2017 | Dar | A61B 5/6803 |
| 2017/0340260 | A1 * | 11/2017 | Chowdhury | A61B 5/14551 |
| 2017/0366213 | A1 * | 12/2017 | Camacho Perez | |
| | | | | A61B 5/02055 |
| 2018/0014783 | A1 * | 1/2018 | Shi | A61B 5/259 |
| 2018/0042491 | A1 * | 2/2018 | Smaill | A61B 5/0215 |
| 2018/0279939 | A1 * | 10/2018 | Madsen | A61B 5/369 |
| 2018/0289949 | A1 * | 10/2018 | Bachinski | A61B 18/1492 |
| 2018/0310854 | A1 * | 11/2018 | Geva | A61B 5/7239 |
| 2018/0321347 | A1 * | 11/2018 | Wang | A61B 5/7203 |
| 2018/0345006 | A1 * | 12/2018 | Ambrose | A61N 1/0476 |
| 2020/0085369 | A1 * | 3/2020 | Vu | A61B 5/398 |
| 2020/0164201 | A1 * | 5/2020 | Berenyi | A61N 1/3603 |
| 2020/0215326 | A1 * | 7/2020 | Wingeier | A61N 1/36034 |
| 2020/0261023 | A1 * | 8/2020 | Werbin | A61B 5/01 |
| 2020/0367781 | A1 * | 11/2020 | Makeyev | A61N 1/04 |
| 2020/0375537 | A1 * | 12/2020 | Carlile | A61B 5/0011 |
| 2021/0023368 | A1 * | 1/2021 | Shakour | A61N 1/3603 |
| 2021/0038092 | A1 * | 2/2021 | Amin | H01L 41/053 |
| 2021/0169417 | A1 * | 6/2021 | Burton | A61B 5/4857 |
| 2021/0177378 | A1 * | 6/2021 | Goericke | G01S 7/521 |
| 2021/0346711 | A1 * | 11/2021 | Ansari | A61N 2/02 |
| 2021/0393955 | A1 * | 12/2021 | Hagedorn | A61B 5/6803 |

OTHER PUBLICATIONS

He, et al., "The Temporal Structures and Functional Significance of Scale-free Brain Activity", Neuron 66, pp. 353-369, May 13, 2010.
He, et al., "Body Surface Laplacian ECG Mapping", IEEE Transactions on Biomedical Engineering, vol. 39, No. 11, Nov. 1992.
Kayser, et al., "Issues and considerations for using the scalp surface Laplacian in EEG/ERP research: A tutorial review", International Journal of Psychophysiology 97 (2015) pp. 189-209.
Kayser, et al., "On the benefits of using surface Laplacian (current source density) methodology in electrophysiology", International Journal of Psychophysiology 97 (2015) pp. 171-173.
Kramer, et al., "Quantitative Approximation of the Cortical Surface Potential From EEG and ECoG Measurements", IEEE Transactions on Biomedical Engineering, vol. 51, No. 8, Aug. 2004.

(56) References Cited

OTHER PUBLICATIONS

Nunez, et al., "Electric Fields of the Brain: The neurophysics of EEG", Chaper 7, pp. 275-312, 'Recording Strategies, Reference Issues, and Dipole Localization', 2006.

* cited by examiner

$$\Phi_c[r,\theta,\phi] = S[rs,\theta,\phi] - \frac{(r-rs)^2 S^{(0,2,2)}[rs,\theta,\phi]}{2rs^2} + \left(\frac{(r-rs)\sigma_g}{\sigma_c} - \frac{(r-rs)^2 \sigma_g}{rs\sigma_c}\right) S^{(1,0,0)}[rs,\theta,\phi] + \ldots$$

Fig. 3

$$\Phi_k[r,\theta,\phi] = S[rs,\theta,\phi] + \left(-1 - \frac{r^2}{2rk^2} + \frac{r}{rk} - \frac{rk}{2rs^2} + \frac{r^2}{rs} + \frac{rk}{rs} - \frac{rk}{2rs}\right) S^{(0,4,4)}[rs,\theta,\phi] +$$
$$\left(\frac{1}{4} + \frac{r^2}{4rk^2} - \frac{r}{2rk} + \frac{r^2}{4rs^2} + \frac{r}{rs} - \frac{rk}{2rks} - \frac{r^2}{rks} - \frac{rk}{2rs^2} - \frac{r^2}{rs^2} + \frac{3r rk}{rs^2} + \frac{2rk^2}{rs^2} - \frac{3r\sigma_c}{rs\sigma_k}\right) S^{(0,2,2)}[rs,\theta,\phi] +$$
$$\left(\frac{3rk\sigma_g}{\sigma_c} - \frac{rk^2\sigma_g}{rs\sigma_c} + \frac{2rs\sigma_g}{\sigma_c} - \frac{9r\sigma_g}{\sigma_c} + \frac{3r^2\sigma_g}{rk\sigma_c} + \frac{6rk\sigma_g}{\sigma_k} + \frac{2r^2\sigma_g}{rk\sigma_k} - \frac{6r rk\sigma_g}{rs\sigma_k} + \frac{4rk^2\sigma_g}{rs\sigma_k}\right) S^{(1,0,0)}[rs,\theta,\phi] +$$
$$\left(\frac{3rs\sigma_g}{\sigma_c} - \frac{3r^2\sigma_g}{2rk\sigma_c} + \frac{r^2\sigma_g}{2rs\sigma_c} + \frac{rs\sigma_g}{\sigma_k} + \frac{r^2\sigma_g}{rk\sigma_k} - \frac{2rrs\sigma_g}{rk\sigma_k}\right) S^{(1,2,2)}[rs,\theta,\phi] + \ldots$$

Fig. 4

| Fig. 5A |
|---------|
| Fig. 5B |

Fig. 5B $$\Phi_x[\theta, \phi] =$$
$$S[9.2, \theta, \phi]$$
$$-0.0953877\, S^{(0,2,2)}[9.2, \theta, \phi] + 0.000030638\, S^{(0,4,4)}[9.2, \theta, \phi] - 7.2545 \times 10^{-10}\, S^{(0,6,6)}[9.2, \theta, \phi]$$
$$-40.4193\, \sigma_g\, S^{(1,0,0)}[9.2, \theta, \phi] + 0.0139727\, \sigma_g\, S^{(1,2,2)}[9.2, \theta, \phi] - 5.88539 \times 10^{-7}\, \sigma_g\, S^{(1,4,4)}[9.2, \theta, \phi] + \ldots$$

ELECTROGRAPHY SYSTEM EMPLOYING LAYERED ELECTRODES FOR IMPROVED SPATIAL RESOLUTION

BACKGROUND

The invention is related to the field of electrography measurement and recording of electro-physiologic activity for diagnostic or other purposes. In more specific applications, the invention is related to the fields of electroencephalography, electrocardiography, and brain-machine interfaces.

The scalp electroencephalogram (EEG) is one of the most common tools used to observe human brain activity. The EEG provides a direct measure of neural activity, with high temporal resolution, and is inexpensive to record. While useful clinically and for research, the EEG suffers from a primary limitation: its poor spatial resolution (i.e., its inability to resolve the activity of two spatially separate brain sources). To address this limitation, two primary approaches have been developed: (1) modeling of brain sources that produce the EEG activity, and (2) a mathematical algorithm to transform the EEG into estimates of radial current flow at the scalp, commonly called the "surface Laplacian", or "current source density (CSD)", or "scalp current density" (SCD). The disadvantage of (1) is the ill-posed inverse problem; an infinite number of brain source configurations could produce an observed EEG. The disadvantage of (2) is that it's mathematically complicated. To compute the surface Laplacian requires computing second-order spatial derivatives of the EEG recorded on the (approximately two-dimensional) cortical surface. However, the surface Laplacian has many benefits, including (i) the estimates are reference-free, (ii) the estimates enhance the spatial resolution of the EEG (i.e., the estimates deblur the EEG), and (iii) the estimates require only modest assumptions about brain structure. The surface Laplacian is considered a state-of-the-art method to deblur the scalp EEG.

SUMMARY

Described herein is a novel method to deblur surface voltage recordings and better approximate activity in deeper layers. Instead of computing only surface derivatives, radial derivatives are computed as well. An electrode configuration is used that senses the brain's electrical activity at a surface (e.g., the standard EEG setup) and at a small distance removed from the surface. From this layered or "electrode stack" configuration both surface and radial derivatives are computed. Theory and simulation indicate that the approach improves spatial resolution of surface voltage recordings compared to the state-of-the-art surface Laplacian approach.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

FIG. 3 is a first equation applied to estimate potential at a first layer;

FIG. 4 is a second equation applied to estimate potential at a second layer;

DETAILED DESCRIPTION

Figure 1:
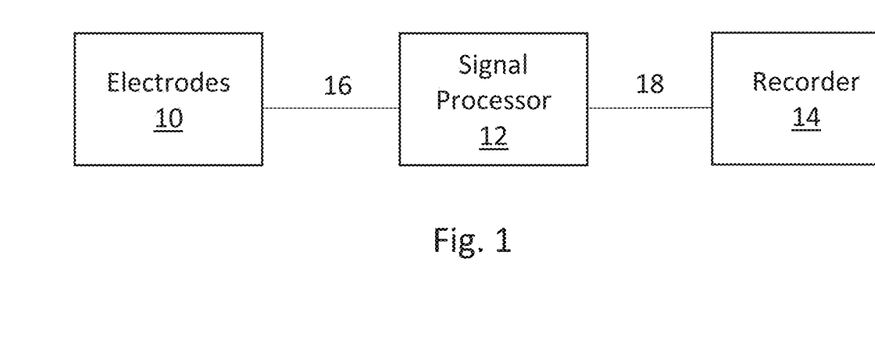
FIG. 1 is a block diagram of an electrography system.

FIG. 1 shows an electrography system including an array of conductive electrodes 10, signal processing circuitry (signal processor) 12, and a recording component (recorder) 14. In use, the electrodes 10 are arranged into two or more spatially separated layers and generate respective electrode signals 16. The electrode signals 16 collectively convey surface-parallel components and surface-orthogonal components of a pattern of physiological electrical activity sensed by the electrodes. In one type of application described in some detail herein, the electrography system is an electroencephalography system used to measure electrical brain activity, and in this application the layers of electrodes are separated/spaced radially, i.e., in the direction perpendicular to the surface of a subject's head. In other uses, different specific arrangements of the electrodes 10 employing spatially separated layers can be employed.

The signal processing circuitry 12 is configured and operative to receive the electrode signals 16 from the electrodes 10 and generate, based on the surface-parallel and surface-orthogonal components, a set of electrography signals 18 representing the pattern of electrical activity being sensed/measured. One key aspect of the signal processing is the use of the surface-orthogonal component in particular to enhance spatial resolution of the electrography signals 18 over that of the raw electrode signals 16.

The recording component 14 is configured and operative to record the electrography signals 18 in a manner enabling application-specific use. Recording can be performed using various media types (e.g., paper, magnetic memory, Flash memory, etc.), and it may be relatively permanent (e.g., paper or long-term magnetic storage) or more ephemeral (e.g., into volatile semiconductor memory). The electrography signals 18 may be further processed in some higher-level manner in some applications, as described more below. However, it will be appreciated that the recorded signal values may be of direct use, such as in a conventional EEG application in which they appear on strips of paper or a display screen to be read and interpreted by a specialist such as a medical clinician, researcher, etc.

Further regarding the signal processing, a Taylor series expansion (TSE) method can be used to approximate a potential across media/tissues having different conductivities and general geometries. In an EEG application for example, the goal is to approximate potentials at the surface of a subject's cerebral cortex, sensing electrical activity from the other side of additional tissues such as skull, scalp, etc. This general aspect is now described in some detail.

Consider the interface between two regions (1 and 2) with locally uniform conductivities $\sigma_1$ and $\sigma_2$, respectively. Define a local orthogonal curvilinear coordinate system with two axes $\xi_\parallel$ parallel to the interface and one axis $\xi_\perp$ perpendicular to the interface. Assume the potential $\Phi_1[\xi_\perp, \xi_\parallel]$ in region 1 is known. A TSE can be written for the unknown potential $\Phi_2[\xi_\perp, \xi_\parallel]$ in region 2:

$$\Phi_2[\xi_\perp, \xi_{//}] = \Phi_1[\xi_\perp^0, \xi_{//}] + (\xi_\perp - \xi_\perp^0)\frac{\sigma_2}{\sigma_2}\partial_{\xi_\perp}\Phi[\xi_\perp, \xi_{//}]\Big|_{\xi_\perp^0} \quad (1)$$
$$-\frac{1}{2}(\xi_\perp - \xi_\perp^0)^2\left(\frac{1}{H}\frac{\partial H}{\partial \xi_\perp}\frac{\sigma_2}{\sigma_2}\partial_{\xi_\perp}\Phi_1[\xi_\perp, \xi_{//}]\Big|_{\xi_\perp^0}\right.$$
$$\left.+\frac{1}{H}\nabla_{//}^2\Phi_1[\xi_\perp, \xi_{//}]\Big|_{\xi_\perp^0}\right) + O\left[(\xi_\perp - \xi_\perp^0)^3\right]$$

where $\xi_\perp^0$ is the location of the interface along $\xi_\perp$; $\nabla_\parallel^2$ includes all derivatives tangential to the interface; and H is a scale factor that depends on the geometry.

Described herein is a layered or stacked electrode configuration enabling computation of a Taylor series expansion in three dimensions at the recording or sensing surface. Derivatives parallel and perpendicular to the recording surface are calculated. To illustrate, the expression $$S[\xi_\perp, \xi_{s\parallel}]$$

is defined as the observed data at the recording surface, corresponding to values of the electrode signals 16. Recordings consist of measurements on the surface and orthogonal to the surface. The values $S[\xi_\perp, \xi_\parallel]$ are used in Equation (1) to estimate $\Phi_b[\xi_\perp, \xi_\parallel]$, the potential below the recording surface, $$\Phi_b[\xi_\perp, \xi_{//}] = S[\xi_\perp^0, \xi_{//}] + (\xi_\perp - \xi_\perp^0)\frac{\sigma_g}{\sigma_b}\partial_{\xi_\perp}S[\xi_\perp, \xi_{//}]\Big|_{\xi_\perp^0} \quad (2)$$
$$-\frac{1}{2}(\xi_\perp - \xi_\perp^0)^2\left(\frac{1}{H}\frac{\partial H}{\partial \xi_\perp}\frac{\sigma_1}{\sigma_2}\partial_{\xi_\perp}\Phi_1[\xi_\perp, \xi_{//}]\Big|_{\xi_\perp^0}\right.$$
$$\left.+\frac{1}{H}\nabla_{//}^2\Phi_1[\xi_\perp, \xi_{//}]\Big|_{\xi_\perp^0}\right) + O\left[(\xi_\perp - \xi_\perp^0)^3\right]$$

where $\sigma_g$ is the conductivity of the device, and $\sigma_b$ is the conductivity below the recording surface. Two important terms in (2) are considered in detail:

1. $S[\xi_\perp^0, \xi_\parallel]$ is the potential recorded at the recording surface, for example the potential recorded at the scalp surface (i.e., the EEG) or from the brain's surface (i.e., ECOG). From these data, the Laplacian tangential to the recording surface $\nabla_\parallel^2\Phi_1[\xi_\perp, \xi_\parallel]|\xi_\perp^0$ can be calculated. These two terms are also accessible in standard brain potential recordings; but in standard brain potential recordings, only derivatives in the two dimensions parallel to the recording surface can be computed.

2. $\partial_{\xi_\perp}S[\xi, \xi_\parallel]|\xi_\perp^0$ is the derivative of the potential orthogonal to the recording surface, evaluated at the recording surface. This term does not appear in standard brain potential recordings. However, using the layered or electrode stack configuration, this term is present and non-zero; and because it can be calculated using the electrode configuration, it can be used to improve the approximation of $\Phi_b[\xi_\perp, \xi_\parallel]$.

Having estimated $\Phi_b[\xi_\perp, \xi_\parallel]$, the application of Equation (1) can be repeated to continue the approximation across other layers, generally of media with different conductivities, if required in the application. This approach is general, and does not necessarily depend on the media properties or geometry; the only requirement is for locally uniform conductivities.

EXAMPLE

EEG Application of the Layered or Electrode-Stack Configuration, Assuming a 4-Shell Spherical Head Model An EEG application of the layered or electrode stack configuration is now described.

Figure 2:
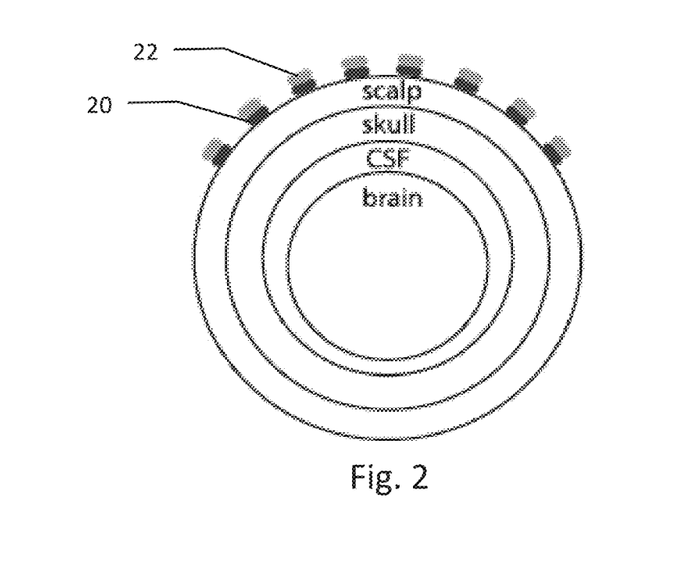
FIG. 2 is a simplified depiction of a spherical 4-shell model with a simple geometry.

FIG. 2 is a simplified depiction of a model with a simple geometry: the 4-shell spherical head model. The 4 shells correspond to the scalp, skull, cerebral spinal fluid (CSF), and brain respectively. Surface electrodes 20 are located directly on the scalp surface. The radial electrode stack includes both the surface electrodes 20 as well as a second layer of electrodes 22, radially displaced from the scalp surface and surface electrodes 20. In this geometry, spherical coordinates are used so that:

$\Phi[\xi_\perp, \xi_\parallel]$ becomes $\Phi[r, \theta, \varphi]$, where $\xi_\perp$ becomes the radius r, and $\xi_\parallel$ becomes the standard angular coordinates $(\theta, \varphi)$; and $$H = r^2$$

In this illustrative example, $S[r, \theta, \varphi]$ is interpreted as the scalp EEG recorded with a layered or electrode stack configuration. In this specific example, the electrodes 10, 20 are aligned radially (also referred to as "stacked"), which in general is not required. The disclosed method utilizes an estimate of the potential both near and away from the surface. The specific example of a radial electrode stack is for ease of presentation.

Given these observed data, the potential within the scalp, skull, and cerebral spinal fluid (CSF) can be approximated to produce an estimate of the potential on the brain surface (i.e., at the interface of the CSF and brain). The approximation requires repeated application of Equation (1). The procedure is now described in some detail.

TSE into the First Layer (Scalp)

Equation (1) is applied to estimate the potential within the scalp $\Phi[r, \theta, \varphi]$ as depicted in the equation in FIG. 3. In this equation, $S[rs, \theta, \varphi]$ is the potential recorded at the surface r=rs; $S(0,2,2)[rs, \theta, \varphi]$ is the second order derivative tangential to the interface (i.e., the surface Laplacian) evaluated at the surface r=rs; $S(1,0,0)[rs, \theta, \varphi]$ is the radial derivative evaluated at the surface r=rs; $\sigma_g$, $\sigma_c$ are the conductivities of the radial electrode stack and scalp, respectively; and " . . . " represents higher order terms. This approximation is valid for values of r within the scalp.

TSE into the Second Layer (Skull)

Equation (1) is applied again, using the estimate of $\Phi_c[r, \theta, \varphi]$, to estimate the potential within the skull $\Phi_k[r, \theta, \varphi]$ as shown in the equation in FIG. 4. In this equation, $S(0,4,4)[rs, \theta, \varphi]$ is the surface biharmonic operator evaluated at the scalp surface r=rs; $S(1,2,2)[rs, \theta, \varphi]$ is the surface Laplacian of the radial derivative evaluated at the scalp surface r=rs; $\sigma_k$ is the conductivity of the skull; and " . . . " represents higher order terms. This approximation is valid for values of r within the skull.

TSE into the Third Layer (CSF)

Figure 5A:
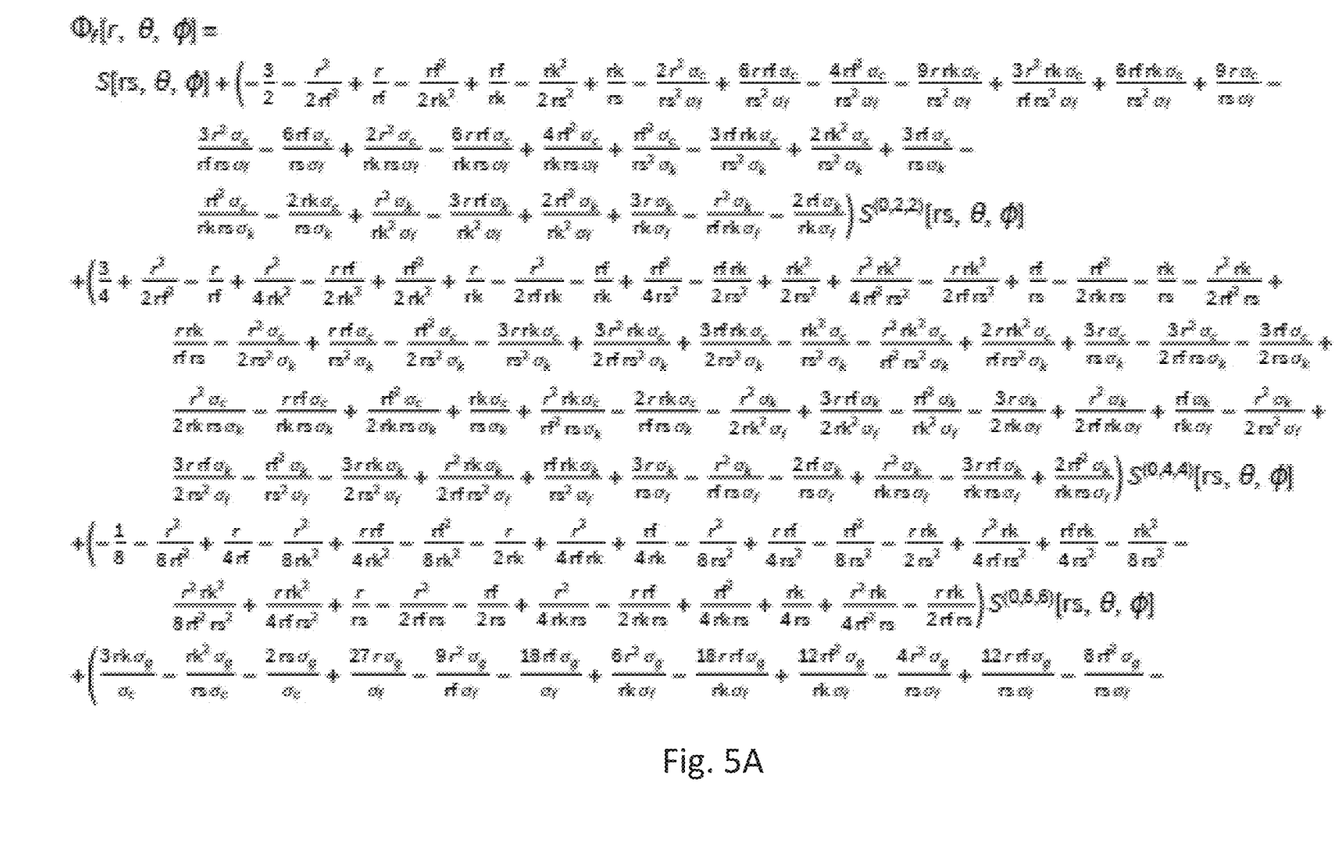
FIG. 5 (consisting of FIGS. 5a and 5b as shown) is a third equation applied to estimate potential at a third layer.

Equation (1) is applied again, using the estimate of $\Phi_k[r, \theta, \varphi]$, to estimate the potential within the CSF, $\Phi_f[r, \theta, \varphi]$, as shown in the equation in FIG. 5 (extending across FIGS. 5a and 5b). In this equation, $S(0,6,6)[rs, \theta, \varphi]$ is the surface triharmonic operator evaluated at the scalp surface r=rs; $S(1,4,4)[rs, \theta, \varphi]$ is the surface biharmonic operator applied to the radial derivative evaluated at the scalp surface r=rs; $\sigma_f$ is the conductivity of the CSF; and " ... " represents higher order terms. This approximation is valid for values of r within the CSF.

TSE to Approximate the Potential at the Cortical Surface

To approximate the potential on the brain surface, $\Phi_b[\theta, \varphi]$, $\Phi_f[r, \theta, \varphi]$ is evaluated at the CSF/brain interface corresponding to radius $r=rb$, $$\Phi_x[\theta, \varphi]=\Phi_f[rb, \theta, \varphi]. \quad (3)$$

This final result represents the object of interest: an approximation to the potential at the cortex. We note that this approximation depends on physical properties of the system (i.e., the conductivities and the radii of the shells), and on derivatives computed from the surface recording with the layered or electrode stack.

Numerical Illustration

To facilitate understanding of the above expression for $\Phi_x[\theta, \Phi]$, an example is given in which numerical values are substituted for the parameters. The values are chosen to be approximately physically correct. The method does not depend on these specific choices. We fix the radii: rb=8.0; rf=8.2; rk=8.7; rs=9.2; with units cm. The conductivities are fixed as: $\sigma_c=0.5$; $\sigma_k=0.01$; $\sigma_f=2.0$; with units S/m. Then an approximation is found for the brain surface potential as shown in the equation in FIG. 6, where S[9.2,θ,φ] is the potential evaluated at the scalp surface. The third line in this equation includes quantities that can be computed using a standard scalp EEG configuration. The present standard in deblurring the scalp EEG utilizes only one term (S(0,2,2) [9.2, θ, φ]), which is the surface Laplacian. To compute the fourth line requires the layered or electrode stack configuration. The innovative use of the layered or electrode stack configuration allows calculation of these additional terms, and an improved approximation to the brain potential (i.e., a better deblurring). It is noted that in this example, the conductance of the device $\sigma_g$ is left unspecified.

EXAMPLE

Figure 7:
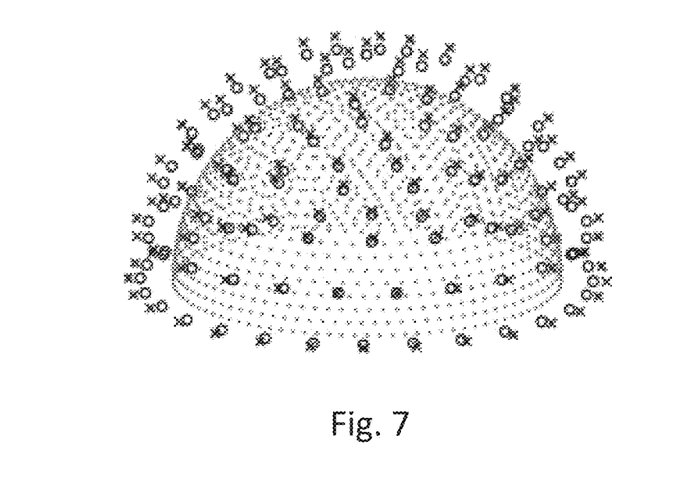
FIG. 7 is a schematic depiction of an example semi-spherical arrangement of an array of electrodes.

Deblurring with a Layered or Electrode Stack Configuration Outperforms the Gold-Standard Method FIG. 7 illustrates a simulation employing the 4-shell spherical model and a large number of sources of activity evenly distributed on the upper half of a sphere located just below the brain surface (radius 7.9 cm). The sources are shown as individual points or dots in FIG. 7. The simulation of an example brain potential recording helps illustrates potential performance of a device as disclosed herein. Sources are simulated to generate pink noise activity, and forward solutions are computed for the potential at the cortical surface (radius 8 cm) and at a layered or electrode stack configuration recording device located on the scalp. For concreteness and ease of presentation, a radial electrode stack is used having two sets of electrodes: 113 inner stack electrodes evenly spaced on the outer scalp sphere (radius 9.2 cm), and 113 outer stack electrodes located at the same angular locations as the inner stack electrodes but radially displaced from the outer scalp sphere (radius Ω>9.2 cm; FIG. 7). In FIG. 7 the inner stack electrodes are indicated by the symbol "o", and the outer stack electrodes by the symbol "x".

Figure 6:
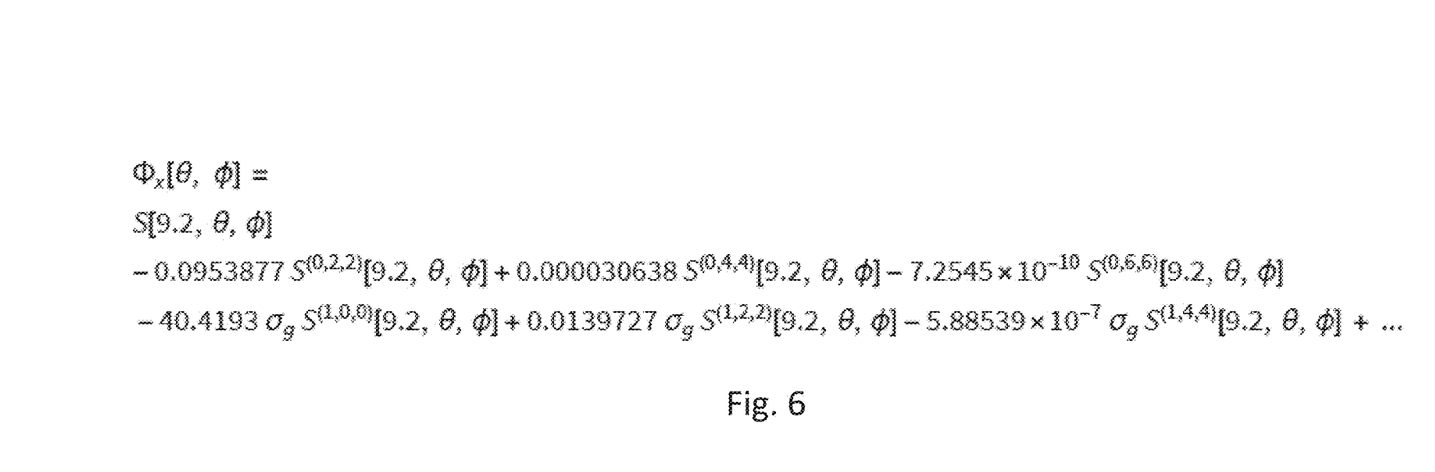
FIG. 6 shows an equation used in a specific numerical example.

From the data recorded at the radial electrode stack, the equation shown in FIG. 6 is used to approximate the cortical potential as:

$$\Phi_x[\theta, \varphi]=S[9.2, \theta, \varphi]-0.0953877\, S^{(0,2,2)}[9.2, \theta\varphi]-40.4193\, \sigma_g S^{(1,0,0)}[9.2, \theta, \varphi]+0.0139727\, \sigma_g S^{(1,2,2)}[9.2, \theta, \varphi]+\ldots$$

where only the radial derivative and surface Laplacian (of the surface voltage and of the radial derivative) are considered, and other terms are ignored. This result can be compared with the most popular existing method to deblur the scalp EEG, the surface Laplacian:

$$SL[\theta, \varphi]=S^{(0,2,2)}[9.2, \theta, \varphi]$$

which simply consists of the surface Laplacian applied to the standard scalp EEG recordings (i.e., only the inner stack electrodes). Computing the surface Laplacian utilizes existing EEG technology consisting of electrodes only on the scalp surface. Generally, deblurring with a layered or electrode stack configuration ($\Phi_x[\theta, \varphi]$) can outperform the gold-standard method (the $SL[\theta, \varphi]$).

Alternative Example

The Radial Derivative Alone Outperforms the Gold-Standard Method

Computing the approximation to the brain surface potential $\Phi_x[\theta, \varphi]$ in Equation 3 requires knowledge of the physical properties of the observed system (e.g., the conductivities, the radii). In some cases, that information may be unavailable. In those cases, the layered or electrode stack configuration can still be used to compute the radial derivative, and this radial derivative alone can be used to approximate the cortical potential. To show this, we continue the simulation of the 4-shell spherical head model described in the previous section.

For this example, we define the radial derivative at the scalp surface as:

$$RD[\theta, \varphi]=S^{(1,0,0)}[9.2, \theta, \varphi]$$

Simulations show that both RD and $\Phi_x[\theta, \varphi]$ produce estimates that match the shape of the cortical potential. Deblurring with a layered or electrode stack configuration using only the radial derivative can outperform the gold-standard method (the SL). The advantage of RD is that it is simple to compute, and does not require knowledge of the physical properties of the observed system (e.g., the conductivities, the radii). However, the RD only matches the shape of the cortical potential, and does not match the magnitude of the cortical potential. The more complete approximation for the brain surface potential in Equation (3) estimates both the shape and the magnitude of the cortical potential. Using $\Phi_x[\theta, \varphi]$ in Equation (3) may be the superior method when the physical properties of the observed system are known.

Example Application

Resolution of Cardiac Electrical Events from the Body Surface

To illustrate the layered or stacked sensor configuration and full Laplacian (FL) method in a specific example, we considered simulations of brain activity. However, we note that the same approach applies in other scenarios to deblur observed surface potentials. For example using voltage sensors placed on the chest surface, one could estimate the cardiac potential at the heart (i.e., generate an electrocardiograph (ECG)). While the physical parameters would differ (e.g., the conductances and layers between the chest surface and heart) the general theory is the same.

The stacked sensor configuration and FL method can be used to deblur other surface potentials recorded in other biological scenarios, for example the cardiac potential.

Example Application

Brain Controlled/Monitoring Technology

Commercial EEG systems are now used for many practical and entertainment applications, including:
- brain controlled technology/brain computer interfaces (e.g., to control high-tech prosthetic limbs, motorized wheel chairs, and entertainment devices).
- monitoring of brain state/feedback devices to enhance performance (e.g., to train athletes or pilots to improve attention).

The layered or stacked sensor configuration and FL method could be incorporated into these technologies, to enhance the resolution of the signal observed, and thereby enhance device performance and impact. The stacked sensor configuration and FL method can be used to enhance existing brain controlled/monitoring technology.

In the examples above, specific instances of the layered or stacked sensor configuration and FL method are described. Beyond these specific examples, the same approach has broad applicability. The same approach—recording with a layered or stacked sensor configuration and FL method—is applicable to voltage recordings from any collection of conductive surfaces. A layer or stacked electrode configuration on the outermost surface can be applied to deblur activity in deeper layers. The conductive surfaces could be biological (e.g., the brain or the body) or synthetic (e.g., conductive materials). The activity could be biological (e.g., cells) or synthetic (e.g., a man-made current source). While the physical parameters would differ (e.g., the conductances and layers geometries) the theory is the same.

Figure 8:
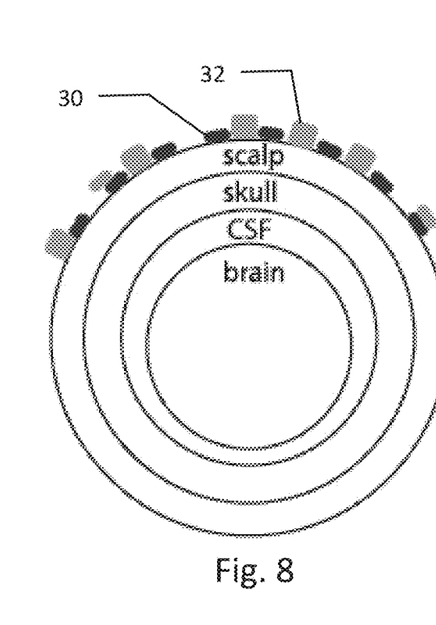
FIG. 8-10 are simplified depictions of alternative electrode arrangements.
Figure 9:
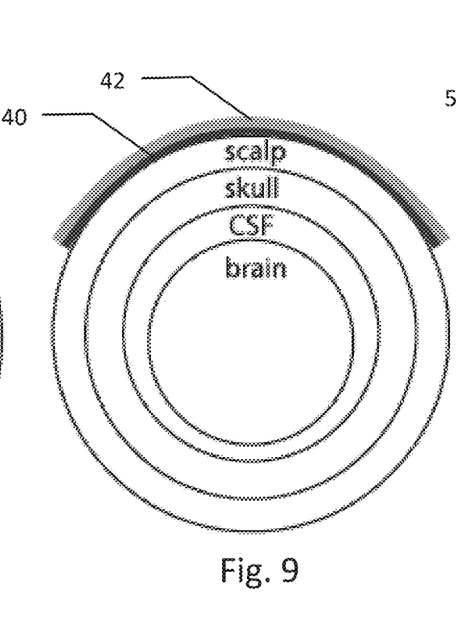
Figure 10:
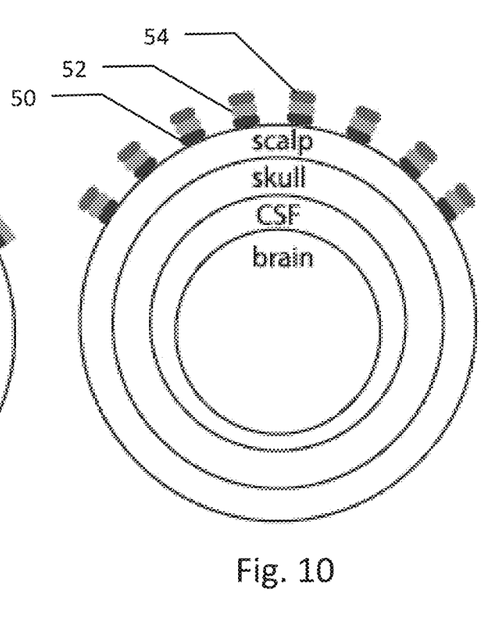

The stacked sensor configuration and FL method can be used to deblur surface potentials in conductive media, both biological and synthetic. To illustrate a sensor configuration and FL method in a specific example, we considered voltage sensors stacked radially (e.g., FIG. 2). However, other configurations of the electrodes are possible, including the following which are illustrated in FIGS. 8-10 respectively:

Off-axis sensor configuration (FIG. 8): The surface and displaced sensors do not require radial alignment. Instead, all or a subset of the sensors could be displaced, and the number of sensors could vary at each depth. FIG. 8 shows the 4-shell spherical head model with this variation of sensor configuration. Some sensors 30 remain directly on the brain surface, while other sensors 32 extend away from the scalp surface. Some sensors 30, 32 are radially stacked, while others are offset.

Continuous sensor configuration (FIG. 9): The discrete sensors could be replaced by a continuous medium (e.g., a sensing gel) from which surface and radial derivatives can be computed. FIG. 9 shows the 4-shell spherical head model with a continuous sensor configuration. A continuous sheet of recording sensors has near-side sensors 40 contacting the scalp surface, and far-side sensors 42 extending away from the scalp.

Multiple sensor layers configuration (FIG. 10): Additional electrode layers can be used to provide for computation of higher-order derivatives, which can be used to estimate higher-order terms in the Taylor series expansion (Equation 1), and improve estimation accuracy. FIG. 10 shows the 4-shell spherical head model with first electrodes 50 on the scalp surface and two sets of electrodes 52, 54 away from the scalp surface. The sensors in each layer could be radially stacked (as illustrated here), or offset (as in FIG. 8), or continuous (as in FIG. 9).

Other Example Applications

The following is a non-exhaustive list of potential applications of the disclosed system and methods:
- Clinical scalp electroencephalogram (EEG) monitoring.
- Clinical scalp EEG recordings to diagnose epilepsy.
- Clinical scalp EEG recordings in the emergency room to diagnose brain injury, coma.
- Future therapies or biomarkers that require accurate measures of brain activity.
- Invasive electroencephalogram (iEEG) to improve spatial resolution or estimate activity in deeper brain regions.
- Research scalp EEG recordings (e.g., a research lab measuring brain rhythms).
- Commercial EEG systems for brain controlled technology (e.g., https://www.emotiv.com/)
- Commercial EEG systems to control internal state (e.g., meditation, http://www.choosemuse.com/)
- Commercial EEG systems to monitor brain state (e.g., monitor attention)
- Commercial EEG systems to enhance performance (e.g., train athletes or pilots to improve attention)
- Commercial/Clinical/Research EEG systems for Brain Computer Interfaces (e.g., systems that use the EEG to control high-tech prosthetic limbs, motorized wheel chairs).

While various embodiments of the invention have been particularly shown and described, it will be understood by those skilled in the art that various changes in form and details may be made therein without departing from the scope of the invention as defined by the appended claims.

What is claimed is:

1. An electrography system, comprising:
an array of conductive electrodes arranged into two or more stacked electrode layers extending across a surface and being spatially separated in a direction orthogonal to the surface, the electrodes being operative to generate respective electrode signals collectively conveying surface-parallel components and surface-orthogonal components of a pattern of physiological electrical activity sensed by the electrodes at the surface, the surface-parallel components being tangential to the surface and the surface-orthogonal components being orthogonal to the surface;
signal processing circuitry configured and operative to receive the electrode signals and to generate, based on the surface-parallel components and derivatives of the surface-orthogonal components, a set of electrography signals representing the pattern of physiological electrical activity; and
a recording component configured and operative to record the electrography signals in a manner enabling application-specific use thereof.

2. The electrography system of claim 1, wherein respective electrodes of the spatially separated electrode layers are aligned in the direction orthogonal to the surface into a stacked-electrode configuration.

3. The electrography system of claim 1, wherein at least some of the electrodes of the spatially separated electrode layers have an offset configuration in which they are not aligned in the direction orthogonal to the surface.

4. The electrography system of claim 1, wherein the electrodes are configured into two or more continuous sheets for corresponding spatially separated electrode layers.

5. The electrography system of claim 1, wherein the electrodes are arranged into three or more stacked electrode layers that are spatially separated in the direction orthogonal to the surface.

6. The electrography system of claim 1, wherein the signal processing circuitry employs a model of one or more tissue layers between the surface and a source of the physiological electrical activity, and is configured and operative to generate the set of electrography signals by processing including calculation of a Taylor series expansion to approximate a potential at respective inter-layer boundaries and within the tissue layers based on the model.

7. The electrography system of claim 6, wherein the tissue layers have respective distinct conductivities and geometries, and the Taylor series expansion models electrical parameters of the respective layers as they affect sensing of the pattern of physiological electrical activity.

8. The electrography system of claim 7, wherein the tissue layers are animal tissues having respective distinct conductivities and geometries, and the electrical parameters are electrical parameters of the respective animal tissues.

9. The electrography system of claim 8, configured as an electroencephalography system used to record an electroencephalograph, and the animal tissues include at least brain and skull.

10. The electrography system of claim 9, wherein the processing employs a 4-shell spherical model representing brain, cerebrospinal fluid, skull and scalp as respective ones of the tissue layers.

11. The electrography system of claim 9, wherein the processing employs a biologically realistic model of tissue geometry and conductivities.

12. The electrography system of claim 6, wherein the electrodes are arranged into three or more electrode layers separated in the direction orthogonal to the surface, and the Taylor series expansion expresses an iteration of a single-layer Taylor series expansion applied to successive ones of the spatially separated layers.

13. The electrography system of claim 1, configured as an electroencephalography system used to record an electroencephalograph.

14. The electrography system of claim 1, configured as an electrocardiography system used to record an electrocardiograph.

15. The electrography system of claim 1, configured as a component of a human-machine interface in which the electrography signals are interpreted as directing particular actions of a control led machine.

* * * * *